(12) United States Patent
Chaggares et al.

(10) Patent No.: US 9,907,538 B2
(45) Date of Patent: *Mar. 6, 2018

(54) HIGH FREQUENCY ULTRASOUND PROBE

(71) Applicant: FUJIFILM SonoSite, Inc., Bothell, WA (US)

(72) Inventors: Nicholas Christopher Chaggares, Oshawa (CA); Eric Rieder, Ajax (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/441,198

(22) Filed: Feb. 23, 2017

(65) Prior Publication Data

US 2017/0224306 A1 Aug. 10, 2017

Related U.S. Application Data

(63) Continuation of application No. 14/286,918, filed on May 23, 2014, now Pat. No. 9,603,580.

(60) Provisional application No. 61/827,524, filed on May 24, 2013.

(51) Int. Cl.
*A61B 8/00* (2006.01)
*B06B 1/06* (2006.01)

(52) U.S. Cl.
CPC .......... *A61B 8/4494* (2013.01); *A61B 8/4444* (2013.01); *A61B 8/4488* (2013.01); *B06B 1/06* (2013.01)

(58) Field of Classification Search
None
See application file for complete search history.

(56) References Cited

U.S. PATENT DOCUMENTS

| 5,223,741 | A | 6/1993 | Bechtel et al. |
| 8,316,518 | B2 | 11/2012 | Lukacs et al. |
| 9,603,580 | B2 | 3/2017 | Chaggares et al. |
| 2003/0018267 | A1* | 1/2003 | Erikson ................. B06B 1/0622 600/459 |
| 2007/0167820 | A1 | 7/2007 | Hirayama et al. |
| 2007/0293762 | A1 | 12/2007 | Sawada et al. |
| 2008/0002460 | A1 | 1/2008 | Tuckerman et al. |
| 2009/0108708 | A1 | 4/2009 | Jiang et al. |
| 2009/0193874 | A1 | 8/2009 | Cobianu et al. |

(Continued)

FOREIGN PATENT DOCUMENTS

| CN | 101322233 A | 12/2008 |
| CN | 101385392 A | 3/2009 |

(Continued)

OTHER PUBLICATIONS

European Patent Office, Extended European Search Report, EP Patent Application 14801593.6, dated Jan. 30, 2017, 11 pages.

(Continued)

*Primary Examiner* — Joel F Brutus
(74) *Attorney, Agent, or Firm* — Perkins Coie LLP

(57) ABSTRACT

A high frequency ultrasound probe includes a substrate having a number of transducer elements on it and a ground plane that is electrically coupled by one or more vias to a conductive frame that supports the substrate. The conductive frame is electrically coupled to a ground plane of a printed circuit having conductors that are coupled to the transducer elements.

7 Claims, 8 Drawing Sheets

(56) References Cited

U.S. PATENT DOCUMENTS

| | | |
|---|---|---|
| 2009/0278217 A1 | 11/2009 | Laming et al. |
| 2010/0156244 A1 | 6/2010 | Lukacs et al. |
| 2011/0071396 A1 | 3/2011 | Sano et al. |
| 2012/0019106 A1* | 1/2012 | Spigelmyer ........... B06B 1/0292 310/348 |
| 2012/0025335 A1 | 2/2012 | Leclair et al. |
| 2012/0064762 A1 | 3/2012 | Muroi et al. |
| 2012/0098625 A1 | 4/2012 | Martin et al. |
| 2012/0104629 A1* | 5/2012 | Bolognia .............. B81B 7/0064 257/774 |
| 2013/0019702 A1 | 1/2013 | Oberdoerfer et al. |
| 2013/0090561 A1 | 4/2013 | Kusukame et al. |

FOREIGN PATENT DOCUMENTS

| | | |
|---|---|---|
| EP | 1795132 A1 | 6/2007 |
| JP | 08122311 A | 5/1996 |
| JP | 09065490 A | 3/1997 |
| JP | 09222424 A | 8/1997 |
| JP | 09327096 A | 12/1997 |
| JP | 10153586 A | 6/1998 |
| JP | 200029755 A | 11/2000 |
| JP | 2008011494 | 1/2008 |
| JP | 2008109641 A | 5/2008 |
| WO | 2007061216 A1 | 5/2007 |
| WO | 2007103224 A2 | 9/2007 |

OTHER PUBLICATIONS

International Searching Authority, International Search Report and Written Opinion, PCT Patent Application PCT/US2014/039449, dated Oct. 22, 2014, 8 pages.

\* cited by examiner

HIGH FREQUENCY ULTRASOUND PROBE

CROSS-REFERENCES TO RELATED APPLICATIONS

This application is a continuation of U.S. patent application Ser. No. 14/286,918, filed on May 23, 2014, and entitled "HIGH FREQUENCY ULTRASOUND PROBE," which claims benefit of and priority to U.S. Provisional Patent Application Ser. No. 61/827,524, filed on May 24, 2013, and entitled "HIGH FREQUENCY ULTRASOUND PROBE," both of which applications are hereby incorporated by reference herein in their entireties.

TECHNICAL FIELD

The disclosed technology generally relates to the fields of ultrasonic transducers and medical diagnostic imaging. More specifically, the disclosed technology relates to high frequency ultrasonic transducers and corresponding methods of assembly.

BACKGROUND

Ultrasonic transducers provide a means for converting electrical energy into acoustic energy and vice versa. When the electrical energy is in the form of an RF signal, a correctly designed transducer can produce ultrasonic signals with the same frequency characteristics as the driving electrical RF signal. Diagnostic ultrasound has traditionally been used at center frequencies ranging from less than 1 MHz to about 10 MHz. One skilled in the art will understand that this frequency spectrum provides a means of imaging biological tissue with resolution ranging from several mm to generally greater than 300 um and at depths from a few mm down to 10 s of cm.

High frequency ultrasonic transducers are generally ultrasonic transducers with center frequencies above 15 MHz and ranging to over 60 MHz. High frequency ultrasonic transducers provide higher resolution while limiting the maximum depth of penetration, and as such, provide a means of imaging biological tissue from a depth of a fraction of a mm to over 3 cm with resolutions in the 20 um to over 300 um range.

There are many challenges associated with fabricating high frequency ultrasonic transducers that do not arise when working with traditional clinical ultrasonic transducers that operate at frequencies below about 10 MHz. One skilled in the art will understand that structures generally scale down according to the inverse of the frequency, so that a 50 MHz transducer will have structures about 10 times smaller than a 5 MHz transducer. In some cases, materials or techniques cannot be scaled down to the required size or shape, or in doing so they lose their function and new technologies must be developed or adapted to allow high frequency ultrasonic transducers to be realized. In other cases, entirely new requirements exist when dealing with the higher radio frequency electronic and acoustic signals associated with HFUS transducers.

RF electrical interconnections require that some form of transmission line be employed to effectively contain the magnetic fields surrounding the signal and ground conductors. One skilled in the art will appreciate that depending on the frequencies being transmitted, and the length of the conductors, electrical impedance matching and shielding techniques must be employed for optimal performance. One skilled in the art will further appreciate that at lower clinical frequencies, such interconnections are highly developed and available in a wide variety of options to the ultrasound system and transducer designers and that such interconnections typically consist of several components as follows: First, a connection to the ultrasound system, which typically consists of a zero insertion force (ZIF) type or other large format connector; second, the electrical cables running from the system connector toward the transducer (typically microcoaxial transmission lines); third, an interface between the cables and the transducer usually including connectors and/or a printed circuit board; and finally, an interface from the connector or circuit board to each of the transducer elements. This typical set of components is readily available in the industry, with many variations being successfully employed for traditional clinical frequency US transducers.

One skilled in the art will appreciate that some of these components will readily scale to the higher frequencies associated with HFUS and other will not. Micro-coaxial transmission lines are well suited to the higher frequencies associated with HFUS, and many industry standard connector solutions are applicable at the system end as well. Furthermore, one skilled in the art will know that printed circuit boards can be designed to function at orders of magnitude higher frequencies than those required for HFUS. The challenge for electrically interconnecting HFUS transducers to the ultrasound system lies principally in the means of making electrical connections to the actual elements of the HFUS array. These elements are very small, fragile, and often limited to strict thermal budgets so that traditional micro electrical interconnection techniques are not suitable for HFUS transducers. Wire bonding, low temperature soldering, and ACF adhesives for example, are widely used technologies for making interconnections to traditional clinical frequency transducers. However, there are limitations to these techniques that make them generally unsuitable for use on HFUS transducers. For example, one skilled in the art will appreciate that wire bonding of interconnections at pitches less than about 100 um can be challenging, and at pitches below 50 um become nearly impossible. When process temperature are limited to less than about 100 degrees C., wire bonding is even more challenging. In addition, mechanical forces associated with wire bonding become problematic when substrate thickness is less than about 100 um. Typical piezoelectric materials suitable for making HFUS transducers must be thinned to about 100 um down to less than 30 um for transducers spanning the 15 MHz to 50 MHz center frequency range. These thin substrates tend to crack when wire bonding is attempted. ACF tape and other asymmetrical conductive adhesive systems are not suitable for high reliability connections at pitches below about 200 um, and also generally require a thermal budget in excess of 120 degrees Celsius, which one skilled in the art will understand, may problematic for some materials associated with the fabrication of HFUS transducer materials.

Some HFUS transducers currently employ a grounding system that relies on a copper electrode made from thin conductive foil to be electrically attached to the front (lens side) ground plane of the transducer, and then exit the side of the stack and wrap around toward the flex circuits ground planes.

The primary challenge of this approach is related to the spacing of the lens to the ground plane of the piezoelectric material. In the conductive foil design, this space is equal to the thickness of the matching layers between the piezoelectric substrate and the lens, for example, in a three matching layer device, three quarter wave matching layers or about 30 um at 50 MHz up to about 70 um for 20 MHz (for reference, typical printer paper is 100 um thick). This necessitates the use of very thin foil attached to the array ground plane with a very thin bond line of conductive epoxy. Preservation of the mechanical integrity of the foil during subsequent lapping and adhesive/cleaning procedures is very challenging. Other methods might be employed to allow the use of thicker foil, but a secondary limitation of the foil is the risk of causing a delamination of the lens due to forces associated with bending the conductive foil, which are increased as the foil becomes thicker.

Finally, one skilled in the art will recognize that the conductive foil technique requires that the ground electrode exits the stack structure along the edges, making electrical isolation of the device challenging especially when BF or CF medical device ratings are required. Given these problems, there is a need for improved techniques of making connections to high frequency ultrasound transducer elements.

SUMMARY

As will be discussed and illustrated below, the disclosed technology relates to a high frequency ultrasound probe for transmitting and receiving high frequency ultrasound signals and methods of assembling such a probe. The probe comprises a substrate with a plurality of high frequency transducers having a ground electrode on an outer face of the transducers and individually connected signal electrodes on an opposite, inner face of each of the transducers. The probe also includes a plurality of vias created around the perimeter of the transducer substrate material, which are electrically connected to the ground electrode on the front outer side of the substrate containing the arrayed transducers. The probe further includes a support structure of which at least a part is electrically conductive, and which exhibits a coefficient of thermal expansion (CTE) that is closely matched to that of the transducer substrate.

BRIEF DESCRIPTION OF THE DRAWINGS

The invention may be more completely understood in consideration of the accompanying drawings, which are incorporated in and constitute a part of this specification, and together with the description, serve to illustrate the disclosed technology.

DETAILED DESCRIPTION

To address the above mentioned problems, the technology disclosed herein relates to high frequency ultrasound transducers. As will be discussed in further detail below, one embodiment of an ultrasound probe in accordance with the disclosed technology includes a hybrid support structure having an overall coefficient of thermal expansion that is closely matched to that of a substrate material used to make an array of transducer elements. This allows the support structure to be joined to the transducer substrate without inducing significant stress or strain over the thermal excursions routinely seen by ultrasound transducers.

Figure 1:
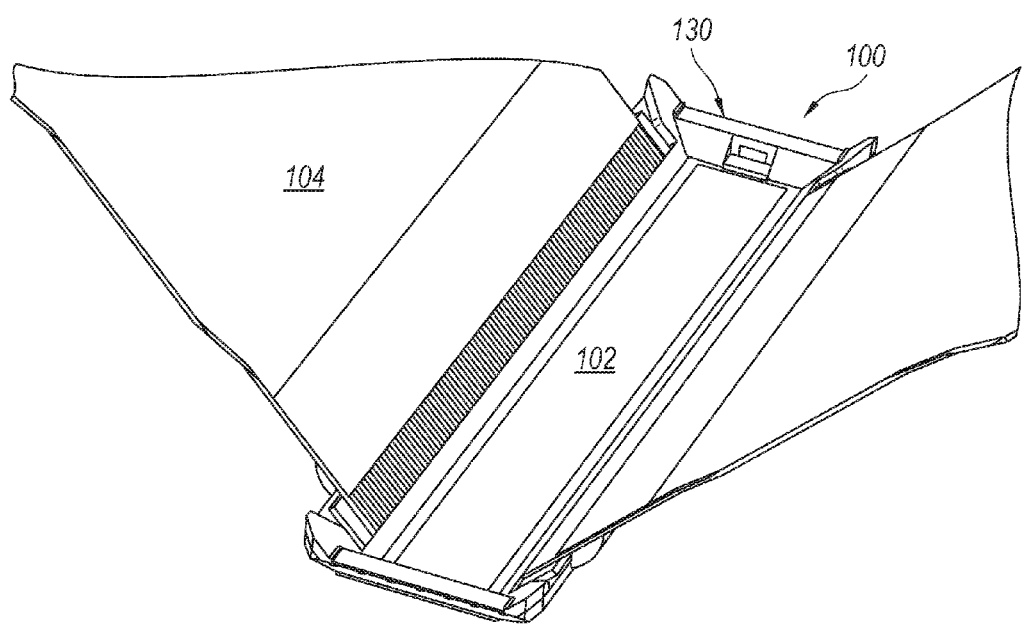
FIG. 1 is an isometric view of the complete assembly of the arrayed transducer labeled to illustrate the components of the grounding system in accordance with an embodiment of the disclosed technology.

In the embodiment shown in FIG. 1, a high frequency ultrasound transducer 100 includes a linear (or other shaped) array of transducer elements 102, a cable bundle 104 containing a plurality of RF transmission lines for carrying RF electrical signals between an ultrasound system (not shown) and the arrayed ultrasound transducer elements, and a plurality of electrical interconnections lying between the RF transmission lines and the arrayed transducer elements. A mechanical housing (not shown) encapsulates some or all of the components included in the ultrasound probe assembly, such as the arrayed transducer elements, an acoustic stack and lens, and the electrical interconnections to the cable bundle.

In one embodiment the electrical interconnections made between the transducer elements 102 and the transmissions lines of the cable bundle 104 are made according to a Laser Etch Laser (LEL) process as described in U.S. Pat. No. 8,316,518 and U.S. patent application Ser. No. 13/657,783 which are herein incorporated by reference in their entirety.

As described in the '518 patent, electrical connections are made between a transducer element and a conductor in a flexible circuit or cable bundle by coating the conductors and transducer elements with a particle (e.g. silica) filled epoxy. The area over the transducer elements is exposed and a low fluence laser is used to create trenches in the epoxy where conductors are desired. The number of laser pulses is increased over portions of the flex circuits in order to dig down to the copper conductors in the flex circuits. The channeled epoxy and the transducer elements are then sputter coated with a conductor such as gold. A resist is then placed over the gold. The resist is then removed with a low fluence laser in areas where the gold is to be removed. A wet etch process is then used to remove most of the gold conductor in the areas where it is not desired. A higher fluence laser is used to remove any remaining gold. The resist that is located over the areas where a conductor is desired is then chemically dissolved.

FUJIFILM Sonosite, Inc. (the assignee of the present applications) developed the Laser-Etch-Laser process (referred to as LEL), which is capable of connecting a standard flexible PCB to an ultrasonic array stack with pitches down to less than 10 um, and within a thermal budget of <80 degrees C. LEL-based technology is currently used in all the VSI designed arrays ranging from 90 um down to 38 um in pitch, and has proven to be very reliable in the field.

In one embodiment, two flex circuits 104 are connected to either side of the transducer array. One circuit has conductors for the odd numbered transducer elements while the other printed circuit has conductors for the even numbered transducer elements. Each printed circuit has conductors with a pitch twice that of the array.

The techniques described in the '783 application are similar except that a stepped flex circuit is used where conductors in different layers of the flex circuit are spaced farther apart than the distance between adjacent electrode elements. The conductors of the flex circuits are interleaved so that connections can be made at a tighter pitch can be made with having all the conductors on the same layer of a printed circuit.

While the disclosed embodiment of the transducer probe includes electrical interconnections made using the LEL technique, one skilled in the art will recognize that electrical interconnections between the signal electrodes of the array and the transmission lines of the conductor bungle could be made by alternative methods if space and thermal budgets permit.

The exemplary high frequency ultrasound probe described herein is designed specifically to address one of the technical challenges specifically associated with making diagnostic images using high frequency ultrasound transducers having a center frequency in the range of at least about 15 MHz and up to about 50 MHz or higher. One skilled in the art will understand that while some state of the art techniques used for making traditional ultrasound probes, having center frequencies between about 1 MHz and 10 MHz, will scale to higher frequencies, others techniques will not. One skilled in the art will also understand that RE transmission lines and grounding techniques must be correctly designed for the frequencies and physical dimensions of a device to provide optimal function, such as minimization of unwanted electrical reflections, maximizing SNR, and providing RF shielding.

In addition to the challenges associated with electrically connecting each element to the conductor that will carry the driving signal to the transducer, there is a need for providing a good RF ground and adequate shielding to the array. One skilled in the art will understand that electrical grounding of an RF device containing many elements, such as an arrayed HFUS transducer, requires specific characteristics of the ground conductors to ensure low cross talk between elements, high SNR and good noise immunity, and broad band performance ensuring good signal integrity. Ground currents must be carried away from adjacent elements through low impedance conductive planes rather than wires, as inductance can cause unpredictable behavior and ground bounce can produce unwanted crosstalk between channels. In addition, one skilled in the art will recognize the need to account for controlled impedance transmission lines and impedance matching as well as EMI shielding, both of which influence good RF ground design.

In the exemplary embodiment described herein, micro machined vias and a ground plane are used to create a low impedance, high quality RF ground in a HF ultrasound transducer. A high frequency ultrasound probe constructed in accordance with the disclosed technology has a high quality, low impedance RF ground plane that is both electrically and spatially efficient and mechanically and thermally robust. One skilled in the art will recognize that each transducer in the scan head can comprise a substrate material consisting of a dielectric electromechanical driver, such as, but not limited to, a piezoelectric ceramic or a ferroelectric relaxor material, a ground electrode adjacent to one face of the driver, and a signal electrode adjacent the opposite face, thus allowing an electric field to be imposed or measured across the thickness of the electromechanical driver. One skilled in the art will also understand that the transducer substrate may also consist of a composite material based on a suitable electromechanical driver material arranged in an advantageous pattern within a matrix of passive dielectric material, such as a polymer, for example an epoxy, to produce an acoustic transducer having properties that are a composite of the driver and matrix materials. One skilled in the art will further understand that this method could readily be applied to any suitable transducer substrate consisting of a dielectric material and having a bounding region for creating vias, or being bounded by a dielectric or insulating material through which vias can be created.

Figure 4:
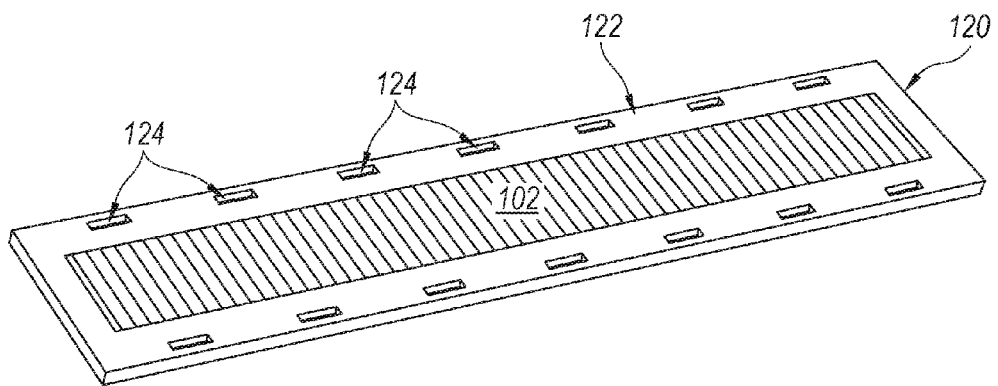
FIG. 4 is a perspective view of the transducer substrate showing the pockets and metal film that will later form the vias in accordance with an embodiment of the disclosed technology.
Figure 5:
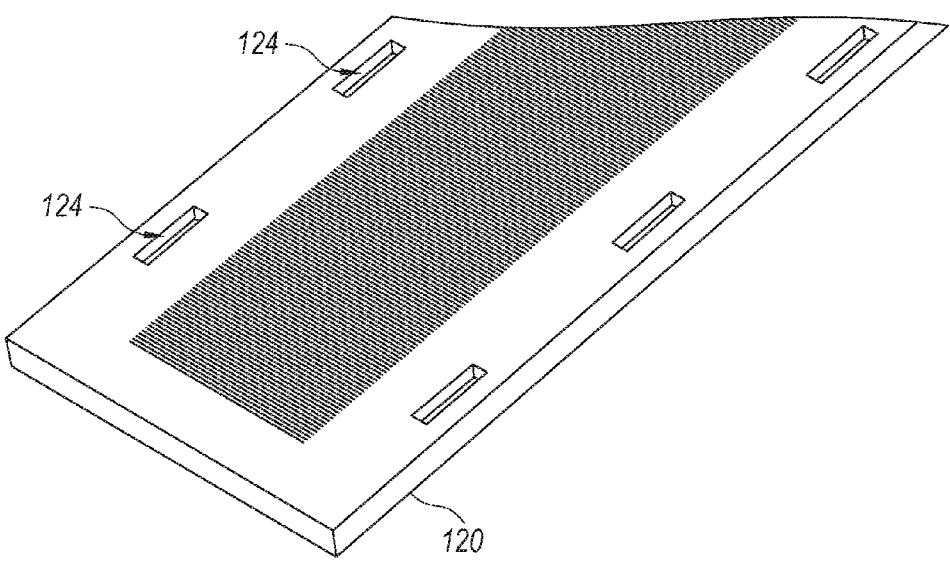
FIG. 5 is a close up perspective view of the via pockets in accordance with an embodiment of the disclosed technology.
Figure 6:
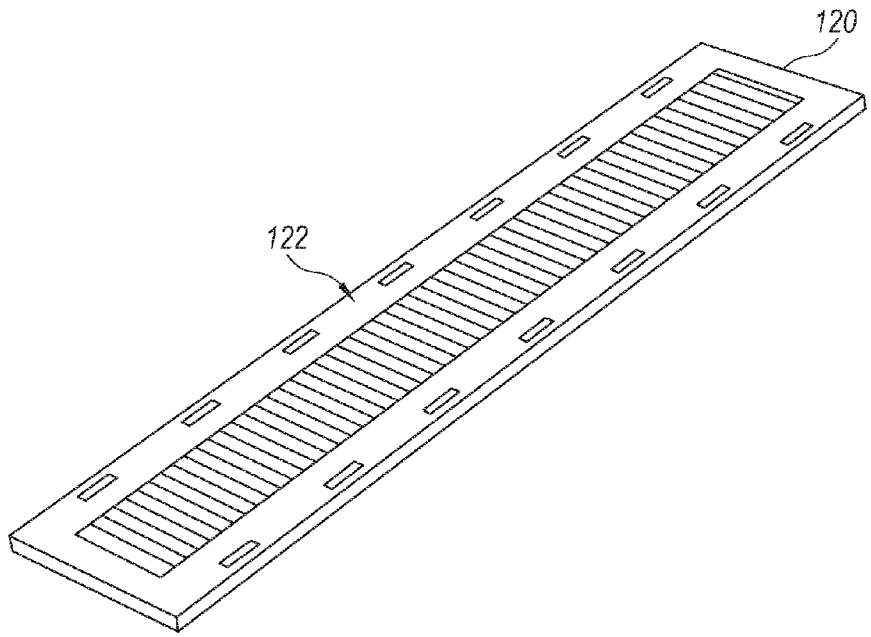
FIG. 6 is a perspective view of the via pockets filled with a conductive epoxy in accordance with an embodiment of the disclosed technology.

In one preferred embodiment, the ground electrode is common to all the transducer elements in the array, and is located on the distal face of the transducers and the substrate from which they are formed. FIGS. 4 and 5 illustrate a transducer substrate 120 in which the transducer elements 102 are formed. One surface (e.g. the outer surface) of the substrate is covered with a conductive material 122 such as gold. The substrate 120 has a number of vias 124 surrounding the perimeter of the substrate. The vias are plated through in order to allow the conductive material 122 on the outer surface of the substrate to make electrical contact with a ground plane on the flex (or other) circuit that holds the transmission lines to drive the transducer elements.

Figure 15:
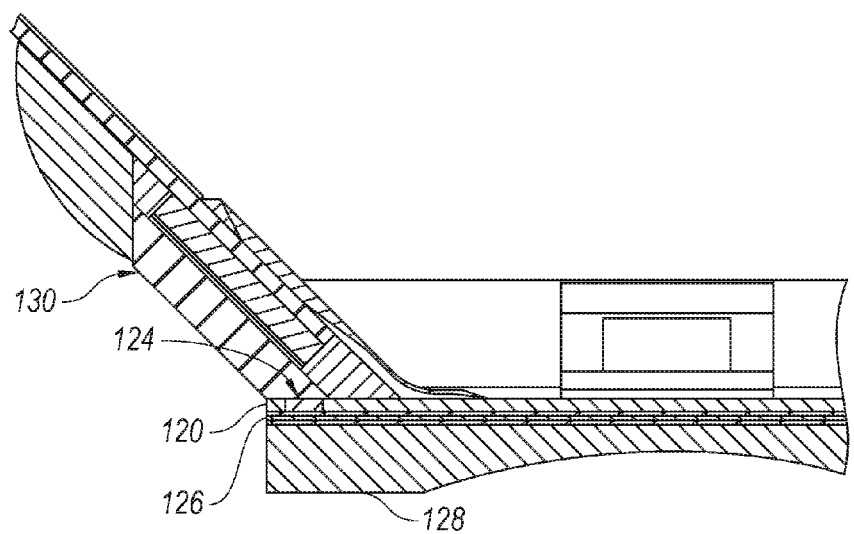
FIG. 15 shows a partial cross section of the arrayed transducer with both the signal electrodes and the ground system in place, illustrating the insulating function of the conductive hybrid support structure.

The conductive material 122 forms a common ground electrode that is overlaid by an acoustic stack typically consisting of one or more matching layers and a lens. FIG. 15 shows a cross-section of an assembled ultrasound probe including substrate 120, the vias 124, a matching layer 126 positioned over the substrate and a lens 128 positioned over the matching layer 126 all of which are secured to a conductive frame 130. One skilled in the art will understand that a variety of acoustic stacks and or lens configurations are possible.

Figure 3:
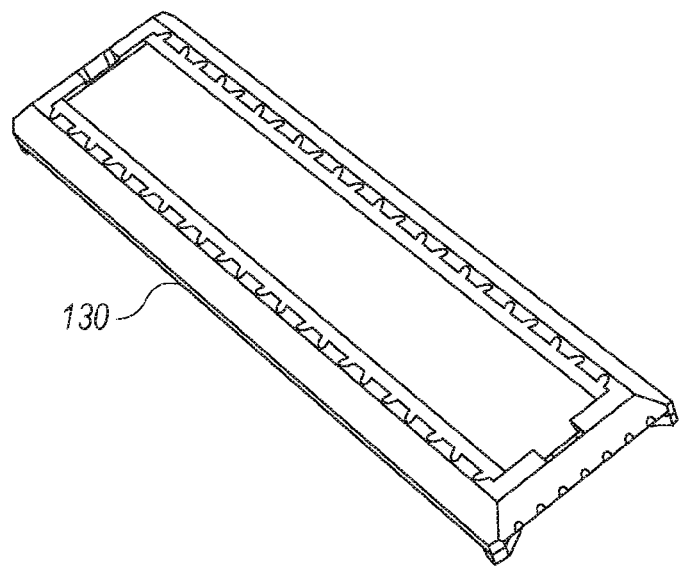
FIG. 3 is a perspective view of the bottom of the conductive hybrid support structure in accordance with an embodiment of the disclosed technology.
Figure 10:
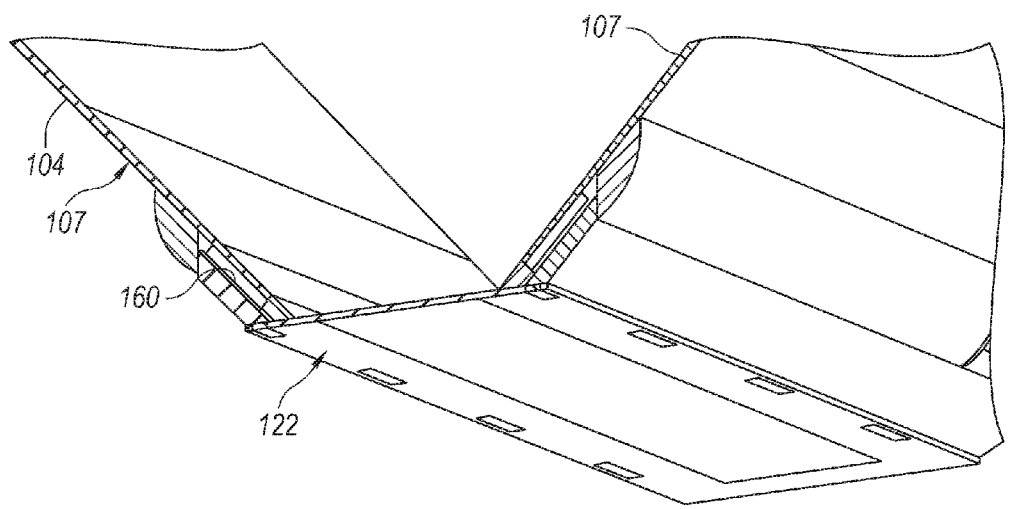
FIG. 10 is a cross section perspective view fully labeled to illustrate the functional parts of the array transducer and the grounding system in accordance with an embodiment of the disclosed technology.

In the exemplary embodiment, the ground plane formed by the conductive material 122 is shown to be on the distal face of the arrayed transducers and to be a common ground plane across the complete array of transducers (See FIG. 4 and FIG. 10). The common planar electrode provides a low impedance path to ground, and provides RF shielding for the signal electrodes located on the proximal face of the array. The ground plane located on the distal face of the transducer substrate is electrically connected to a conductive frame 130 (FIG. 3) by the plurality of conductive vias 124 located along the perimeter of the substrate 120 as shown in FIGS. 4 through 7.

The conductive vias 124 are created by making pockets in the transducer substrate 120 and then depositing an electrode material over the entire outer face of the arrayed transducers, and conformally coating the inner faces of the via pockets 124 as shown in FIGS. 4 and 5. The pockets can be created by any means capable of micromachining ceramics, such as reactive ion etching, laser ablation, or conventional micromachining. In the exemplary embodiment, laser machined vias 124 have slightly tapered walls in the pockets to prevent shadowing during deposition of metal electrodes on the walls of the pockets. The pockets of the vias 124 are then filled with a conductive material, such as conductive epoxy, or any conductive matrix that will adhere to the inner faces of the pocket (see FIG. 6). Finally, during the processing of the arrayed transducers, the transducer substrate 120 is thinned to the required dimension to achieve the required ultrasonic resonance in the transducers, for example, about 30 um for a 50 MHz transducer.

Figure 7:
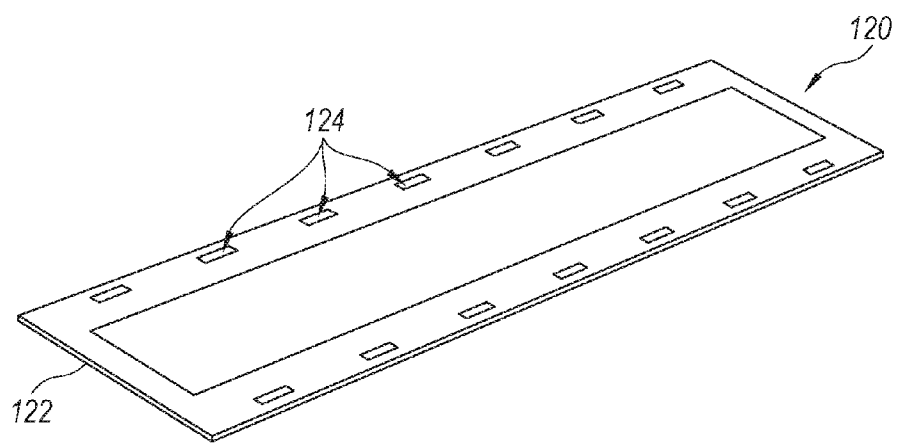
FIG. 7 is a perspective view looking down on the signal side of the transducer substrate that has been thinned to the final thickness and showing the final plated and filled vias as they are exposed from the signal side of the substrate in accordance with an embodiment of the disclosed technology.

By ensuring that the pocket is deeper than the final thickness of the transducer substrate, the vias 124 are fully realized when the transducer substrate is thinned to the final dimension as shown in FIG. 7. By metalizing the vias before filling them with a conductive material, one ensures that expansion/contraction of the conductive filler material does not result in micro cracking around the perimeter of the vias 124

Figure 8:
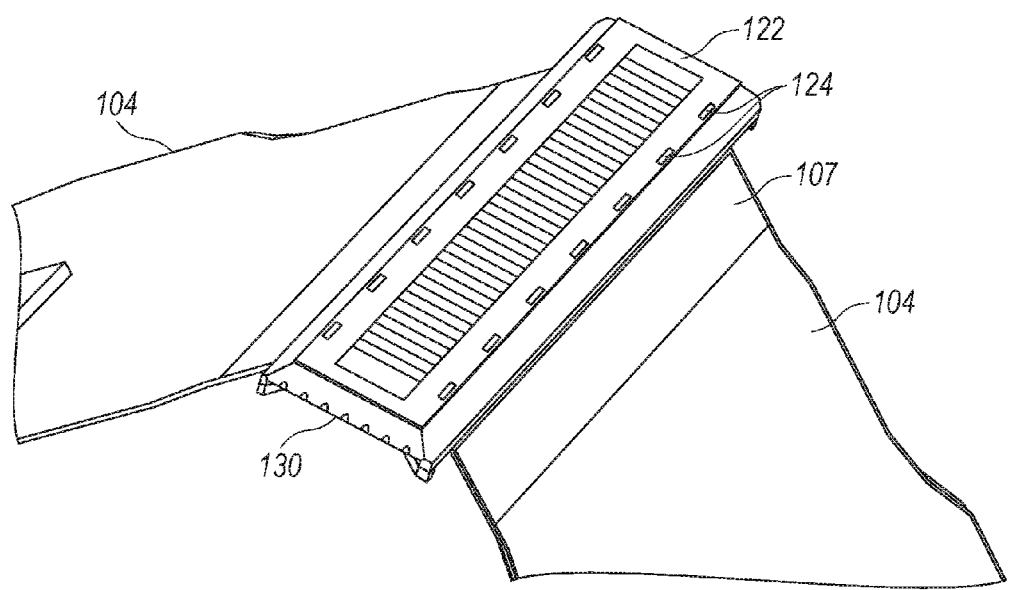
FIG. 8 illustrates the assembled components of the array transducer showing the ground planes of the flex, not yet connected to the conductive support structure in accordance with an embodiment of the disclosed technology.
Figure 9:
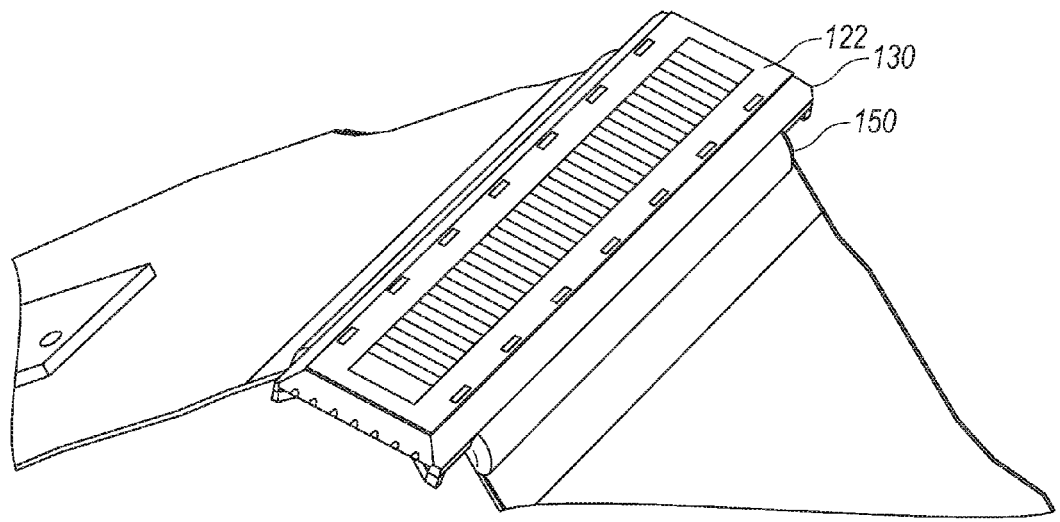
FIG. 9 illustrates the fully assembled array transducer showing the ground path connected by conductive adhesive between the flex circuit ground plane and the conductive support structure in accordance with an embodiment of the disclosed technology.
Figure 11:
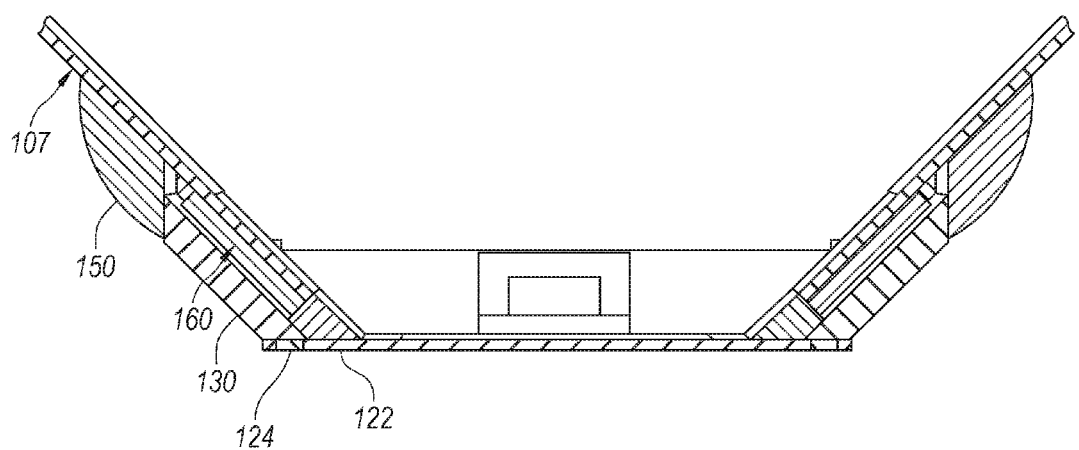
FIG. 11 is a cross section of the grounding system showing the direct path of ground conductors from the common ground plane of the arrayed transducers to the ground plane of the printed circuit board in accordance with an embodiment of the disclosed technology.
Figure 12:
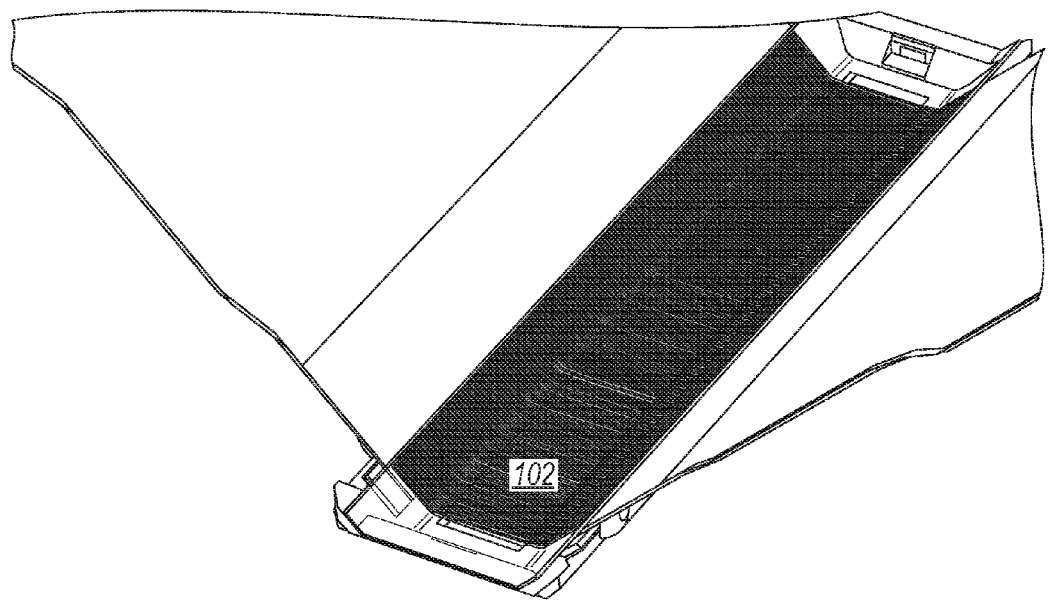
FIG. 12 is a perspective view showing signal interconnections, made using the laser etch laser process, in place in an array transducer in accordance with an embodiment of the disclosed technology.

The conductive frame 130 is then attached to the proximal face of the transducer substrate using a conductive adhesive, so that the exposed conductive bottom face of the hybrid tapered support overlays the exposed upper surface of the conductive vias 124 (see FIGS. 10, 11, and 15). As can be seen in FIGS. 8, 9 and 11, the vias 124 provide a conductive path from the ground plane of the substrate 120 to the conductive frame 130. A conductive adhesive 150 is then used to electrically couple the conductive frame to the ground plane 107 of the flexible printed circuit 104. This ensures a very low inductance connection between the ground plane on the flexible printed circuit and the conductive frame 130 of the hybrid tapered support. It also ensures that the signal electrodes located on the inner surfaces of the transducer substrate, the hybrid tapered support, and the PCBs are completely surrounded by a ground electrode providing excellent shielding.

Figure 2:
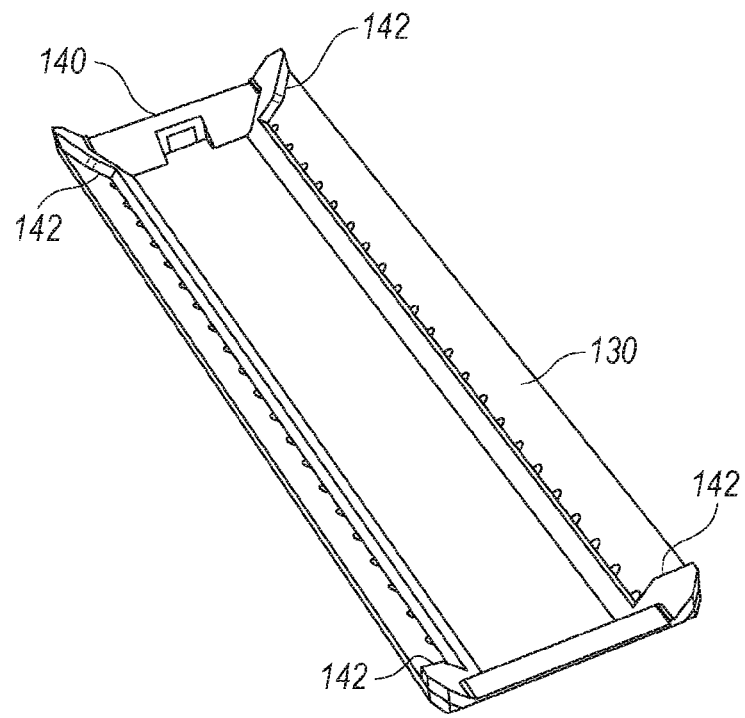
FIG. 2 is a perspective view of the top of a conductive hybrid support structure in accordance with an embodiment of the disclosed technology.
Figure 13:
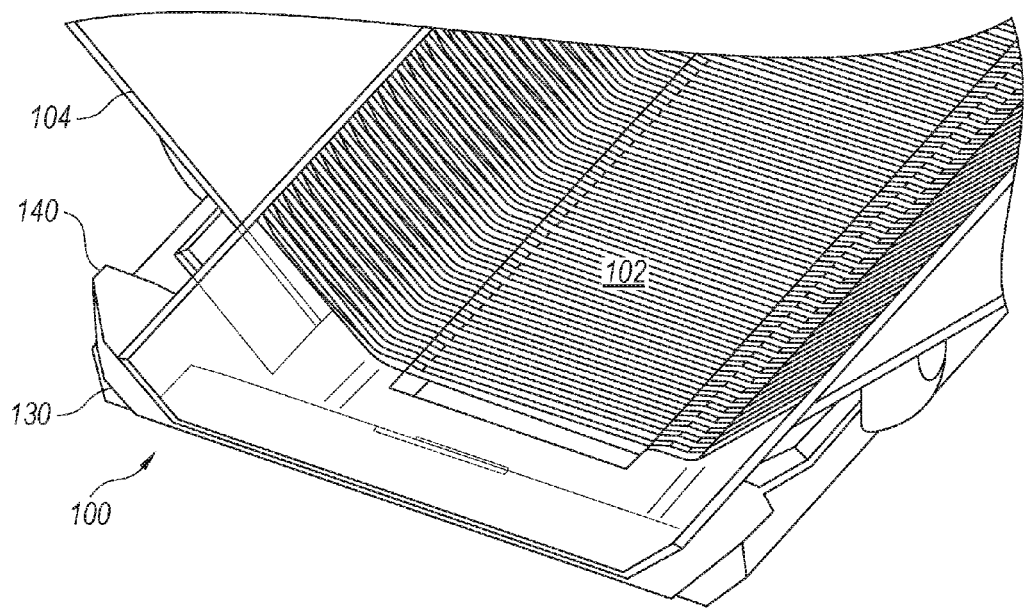
FIG. 13 is a close up perspective view of the signal electrodes at one end of the array showing the need to isolate the signal electrodes from the conductive portion of the support structure used to conduct the ground currents to the ground plane of the flex; in accordance with an embodiment of the disclosed technology.
Figure 14:
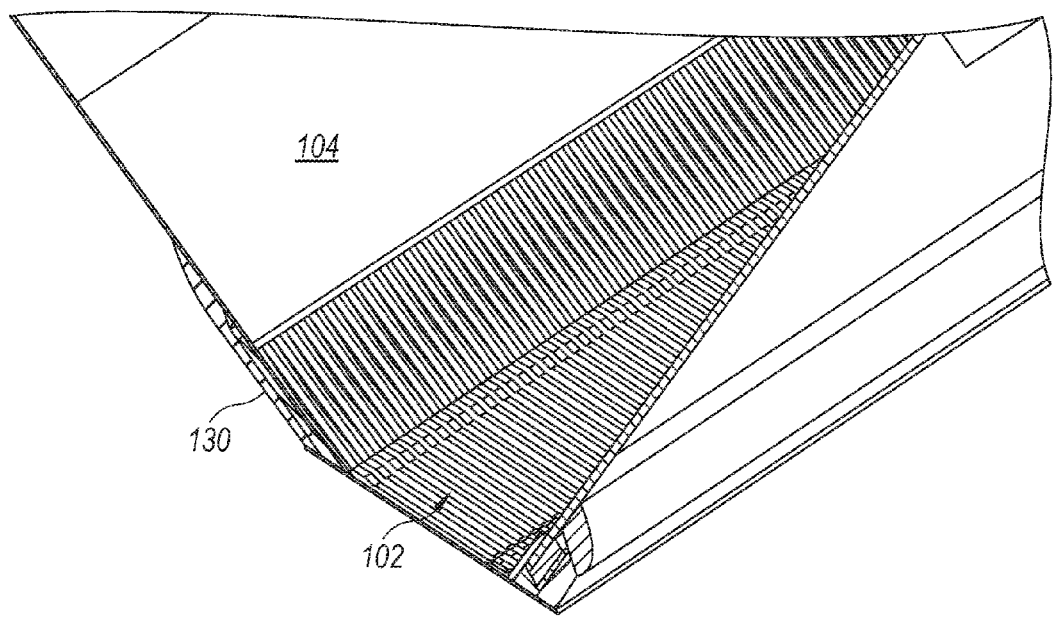
FIG. 14 shows a perspective view of the cross section of the array and signal electrodes in accordance with an embodiment of the disclosed technology.

The conductive frame 130 is part of a hybrid support structure referred to as a hybrid tapered support herein. As shown in FIG. 2, the hybrid tapered support consists of a conductive outer frame 130 and an insulating insert 140 that is secured to the outer frame by over-molding, adhesive or another technique. The insulating insert 140 includes guiding pockets 142 to assist in aligning the printed flexible circuit to the arrayed transducers (see FIGS. 2, 3, and 13). The conductive frame 130 is designed to have a coefficient of thermal expansion that closely matches that of the transducer substrate 120. In an exemplary embodiment, in the case of a ceramic substrate, such as PZT or PMN-PT, molybdenum is chosen for the conductive frame, having a CTE of about 4.8 ppm/degree C. compared to 4.7 ppm/degree C. for PZT. Depending on the expected thermal perturbations that the arrayed transducers are to undergo, a closer CTE match may become more or less important, allowing the choice of different materials. For example, one might also choose engineered nickel iron alloys such as invar and it variants designed to match the CTE of specific materials. Other conductive materials such as graphite based materials, or plated ceramics could also be suitable so long as the CTE of the frame is closely matched to the transducer substrate over the expected thermal range.

As best shown in FIG. 10, the ground electrode 122 is further extended through the conductive support frame 130 to the ground plane 107 of a flexible printed circuit board 104. The connection to the ground plane is made over a large surface to ensure a low impedance connection to the ground plane. In the exemplary embodiment, conductive adhesive is used to connect the conductive support frame 130 to the ground plane 122 of the transducer substrate 120 (see FIGS. 8 through 10), although one skilled in the art will understand that alternative methods of connecting the conductive frame to the ground plane could be used, such as soldering, conductive tapes, metallization etc.

As discussed above, a plurality of signal electrodes are deposited on the proximal face of each transducer, isolated from each other so that each individual transducer in the array can be independently connected to a transmitter/receiver. Each signal electrode is connected to a signal trace located on the signal layer of the flexible printed circuit board, as a means of providing an electrical interconnection between the transducer electrode, and the transmission line cables that carry electrical signals to and from the ultrasound system. As described above, the insulating insert 140 that is secured to the conductive frame 130 provides a non-conductive barrier between the transducer elements 102 and the conductive frame 130.

Furthermore, in order to ensure that laser micromachining of the signal electrodes is possible without risk exposing sections of the conductive frame through the PCB during laser definition of the electrodes, a thin layer of a barrier strip formed of a ceramic insulator 160 such as alumina, is bonded to the back face of the PCB 104 before bonding the PCB 104 into the pocket on the hybrid tapered support (see FIGS. 10 and 11). This insulator 160 serves to stiffen and flatten the flexible PCB prior to alignment in to the tapered support making alignment of signal electrodes in the PCB to the arrayed transducers more efficient and accurate. In addition, the ceramic insulator prevents the creation of short circuits between the traces of the printed flex circuit and the conductive frame 130

One skilled in the art will understand that a conductive frame surrounding the entire perimeter of the arrayed transducer structure will provide additional RF shielding. Furthermore, the use of a conductive ground structure with a high surface area to volume ratio ensures low inductance, and when it is placed in close proximity to all of the array signal conductors ensures minimal impedance for ground currents and therefore better noise rejection compared to using wires to connect the ground from the transducer to the printed circuit ground.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A high frequency ultrasound probe comprising:
   a conductive frame having a coefficient of thermal expansion that is matched to a piezoelectric transducer substrate;
   a piezoelectric transducer substrate having a number of transducer elements that is secured to the conductive frame;
   a ground plane on a distal side of the piezoelectric transducer substrate that is electrically coupled by one or more vias extending through the piezoelectric transducer substrate around a perimeter of the transducer elements to the conductive frame.

2. The high frequency ultrasound probe of claim 1, further comprising one or more printed circuits having conductors that are coupled to the transducer elements and a ground plane, wherein the ground plane of the one or more printed circuits is electrically coupled to the conductive frame.

3. The high frequency ultrasound probe of claim 2, wherein the ground plane of the one or more printed circuits is electrically coupled to the conductive frame with a conductive adhesive.

4. The high frequency ultrasound probe of claim 2, further comprising a non-conductive barrier strip positioned between conductors of the one or more printed circuits and the conductive frame.

5. An ultrasound transducer, comprising:
   a piezoelectric substrate having a number of transducer elements formed therein, wherein the piezoelectric substrate has a common ground electrode on a distal surface of the piezoelectric substrate and a number of vias extending through the piezoelectric substrate and around a perimeter of the transducer elements and that are filled with a conductive material;
   a conductive frame secured to the piezoelectric substrate with a conductive adhesive, wherein the conductive frame is electrically connected to the common ground electrode on the distal surface of the piezoelectric substrate through the vias.

6. The ultrasound transducer of claim 5, wherein the piezoelectric substrate and the conductive frame have similar coefficients of thermal expansion.

7. The ultrasound transducer of claim 5, wherein the conductive frame has sloped walls configured to support conductors to the transducer elements.

* * * * *

UNITED STATES PATENT AND TRADEMARK OFFICE
CERTIFICATE OF CORRECTION

PATENT NO. : 9,907,538 B2
APPLICATION NO. : 15/441198
DATED : March 6, 2018
INVENTOR(S) : Nicholas Christopher Chaggares et al.

It is certified that error appears in the above-identified patent and that said Letters Patent is hereby corrected as shown below:

In the Specification

In Column 5, Line 67, delete "RE" and insert -- RF --, therefor.

In Column 7, Line 5, delete "and or" and insert -- and/or --, therefor.

In Column 7, Line 44, delete "124" and insert -- 124. --, therefor.

In Column 8, Line 57, delete "130" and insert -- 130. --, therefor.

Signed and Sealed this
Tenth Day of July, 2018

Andrei Iancu
*Director of the United States Patent and Trademark Office*